United States Patent [19]

Urban et al.

[11] Patent Number: 4,536,338

[45] Date of Patent: Aug. 20, 1985

[54] PROCESS FOR MANUFACTURE OF FATTY ACID ESTERS OF HYDROXY SULFONATES

[75] Inventors: Warren J. Urban, River Vale; Joseph Barillo, Glen Rock; Jerry J. Krupa, Rockaway, all of N.J.

[73] Assignee: Lever Brothers Company, New York, N.Y.

[21] Appl. No.: 550,274

[22] Filed: Nov. 9, 1983

[51] Int. Cl.$^3$ .................... C07C 143/90; C11D 1/28
[52] U.S. Cl. .................................................. 260/400
[58] Field of Search ....................................... 260/400

[56] References Cited

U.S. PATENT DOCUMENTS

| | | |
|---|---|---|
| 1,860,092 | 5/1932 | Graves . |
| 3,320,292 | 5/1967 | Cahn et al. . |
| 3,383,396 | 5/1968 | Cahn et al. . |
| 3,420,857 | 1/1969 | Holland et al. . |
| 3,420,858 | 1/1969 | McCrimlisk . |
| 4,369,144 | 1/1983 | Lamberti et al. . |
| 4,405,526 | 9/1983 | Lamberti et al. . |

OTHER PUBLICATIONS

"Organic Reactions with Boron Fluoride. XX. Acidolysis of Esters", J. Amer. Chem. Soc., vol. 60, pp. 654–658, (1938).

*Primary Examiner*—Helen M. S. Sneed
*Attorney, Agent, or Firm*—Milton L. Honig; James J. Farrell

[57] ABSTRACT

A method is disclosed for preparing fatty acid isethionate soaps through direct esterification wherein the catalyst is quenched by an alkaline compound at the end of the esterification. Quenching inhibits transesterification between isethionate and later added stearic acids. Transesterification is undesirable impairing lather and bar soap firmness. The traditional stripping of lower molecular weight fatty acids is no longer necessary where low ratios of fatty acids to isethionates are utilized. Alternatively, stripping can be avoided with traditional molar ratios provided water co-distillate fatty acid is not recycled. Finally, it has been shown that zinc catalyzed reactions provide optimum yield and low corrosion at pH about 2.0 to 2.5.

11 Claims, No Drawings

PROCESS FOR MANUFACTURE OF FATTY ACID ESTERS OF HYDROXY SULFONATES

BACKGROUND OF THE INVENTION

1. Field of the Invention

The invention concerns the preparation of surface active agents. In particular, the invention pertains to the use of a catalyzed process for the preparation of directly esterified fatty acyl isethionates (DEFI) formed through the reaction of the alcohol $HOR'SO_3M$ with the organic acid $RCOOH$. DEFI has the formula $RCOOR'SO_3M$ where R is a $C_5$–$C_{18}$ alkyl group, R' is selected from the group consisting of divalent $C_2$–$C_4$ alkylene, $C_6$–$C_8$ aryl and $C_7$–$C_8$ alkylaryl radicals, and M is an alkali metal cation.

2. The Prior Art

Sodium acyl coconut isethionate esters are major ingredients in many commercial soap bars. Synthesis of these esters by direct esterification has been described in U.S. Pat. Nos. 3,320,292, 3,420,857 and 3,420,858. Typically therein, sodium isethionate is reacted with an excess of coconut fatty acids in the presence of a zinc oxide catalyst. Excess fatty acid is required to maintain high reaction rates, fluidity and suppress foaming. As the reaction proceeds, water, a reaction by-product, distills off alongside a considerable portion of fatty acids. Steam distilled fatty acids are collected and may be recycled to the reaction vessel. Recycling prevents deprivation of fatty acid in the reaction mass. Upon completion of esterification, excess coconut fatty acid is removed by distillation. In the removal of coconut fatty acid, a certain amount of stearic acid is added to the reactor vessel to assist stripping of the more volatile coconut acids. Stearic acid remains behind. It imparts the useful properties of firmness, mildness and lather creaminess to toilet bars.

DEFI in which the fatty acids combined are all coconut derived will produce high lather volume. Where DEFI is formed primarily from high molecular weight fatty acids, e.g., stearic acid, the product lathers poorly. Accordingly, transesterification between coconut isethionate ester and stearic acid is to be avoided. For this reason, stearic acid is added as a distillation chaser only towards the end of the coconut acid esterification with isethioniate and not with the initial charge.

Substitutes for the traditional zinc oxide catalyst which would increase reaction rates are highly desirable. With zinc oxide, rates are hastened only by the increase in catalyst concentration. Unfortunately, increased levels of zinc oxide impart a gritty, sandy feel to the toilet bars.

Recently, Lamberti et al disclosed in U.S. Pat. No. 4,405,526 a type of new "fast" catalyst for the DEFI process. These compounds are formed from a mixture of zinc oxide and organic sulfonic acids. High conversions in relatively short amounts of time are therewith achievable. Unfortunately, the transesterification problem is thereby magnified.

Besides the search for faster catalysts and methods to avoid transesterification, an additional problem concerns controlling excess coconut fatty acids. Surplus acids impair the hardness of soap bars. Moreover, excess coconut acids are to be minimized from a cost perspective.

Another desirable goal in the preparation of DEFI is limitation in the number of processing steps. Time, equipment and thereby costs could well be reduced.

Accordingly, it is an object of this invention to inhibit transesterification between higher fatty acids and coconut isethionate esters.

A further object of this invention is to disclose better catalysts for the DEFI process.

Another object of the invention is to reduce the amount of excess coconut fatty acids needed in the DEFI process.

A still further object of this invention is to reduce the number of steps involved in the DEFI process.

SUMMARY OF THE INVENTION

A method is disclosed for preparing a compound of the formula $RCOOR'SO_3M$, wherein R is a $C_5$–$C_{18}$ alkyl group, R' is selected from the group consisting of divalent $C_2$–$C_4$ alkylene, $C_6$–$C_8$ aryl and $C_7$–$C_8$ alkylaryl radicals and M is an alkali metal cation, the process comprising:

(a) heating a first mixture of $C_5$–$C_{16}$ monocarboxylic acid with a hydroxy sulfonate of the formula $HOR'SO_3M$, in a mole ratio of 1.01:1 to 2:1, in the presence of a catalyst;

(b) removing liberated water of esterification from the reaction mass and when the desired conversion to $RCOOR'SO_3M$ is achieved;

(c) quenching the catalyst with an effective amount to neutralize the catalyst of an alkaline compound; and (d) adding a higher molecular weight $C_{15}$–$C_{24}$ fatty acid to the reaction mixture subsequent or simultaneous with addition of the alkaline catalyst quencher.

During removal of liberated water in step (b), there may be continuously supplied to the reaction mass during the course of esterification, a mixture of free $C_5$–$C_{16}$ fatty acids at the approximate rates and proportions at which fatty acids are vaporized.

A further refinement of this process involves the elimination of the traditional stripping step whereby excess free $C_5$–$C_{16}$ fatty acids are removed from the reaction mixture once the desired conversion to $RCOOR'SO_3M$ has been achieved. In one embodiment, the initial mole ratio of $C_5$–$C_{16}$ monocarboxylic acid to hydroxy sulfonate is lowered to 1.01:1 to 1.19:1 and recycling of co-distilled free $C_5$–$C_{16}$ fatty acids is practiced. In an alternate embodiment, the traditional mole ratio of $C_5$–$C_{16}$ monocarboxylic acid to hydroxy sulfonate of 1.35:1 to 1.5:1 or higher is maintained but recycling of co-distilled free fatty acids is not practiced.

Catalysts for the reaction include multivalent metal ion salts, strong acids, acidified zinc oxide, soluble zinc salts and combinations thereof.

When zinc catalysts are utilized, yields are optimized where the reaction pH is maintained from 2.5 or lower. Metal corrosion becomes a problem below about pH 2.0.

DETAILED DESCRIPTION OF THE INVENTION

It has been discovered that the addition of an alkaline material to the reaction mass after completion of coconut acid esterification will prevent unwanted transesterification between coconut isethionate ester and stearic acid. Alkaline materials are believed to quench the reaction by neutralizing the acidic catalyst. Transesterification is halted or greatly reduced. Where soluble zinc is the catalyst, alkaline treatment converts the zinc compound to an oxide with lower catalytic activity.

Addition of catalyst neutralizing compound is preferably coincidental with the addition of stearic or other high molecular weight fatty acids during stripping. However, the alkaline compound may alternatively be added at any time after reaction, prior to or during addition of stearic acid.

In addition to preventing transesterification, catalyst neutralization also serves to reduce corrosion in stainless steel reactors.

Sodium or potassium hydroxides or ammonia are especially preferred quenchers. However, other alkaline materials are useful including inorganic carbonate and bicarbonate salts.

Alkaline quenching materials are utilized in an amount effective for neutralizing the esterification catalyst. Typical concentrations range from about 0.01% to 5%. Preferably, the alkaline quenching material is present from about 0.1 to about 0.5% by weight of total reactants.

A wide variety of catalysts can be employed with the present reaction. Suitable catalysts include multivalent metal ion salts of organic or inorganic compounds, strong acids and mixtures thereof. Zinc oxide, the conventional catalyst, can be utilized in this invention. However, faster acting catalysts are preferred. Among the fast organic catalysts is zinc isethionate. Especially preferred inorganic zinc compounds are those selected from the group consisting of zinc sulfate, zinc sulfamate, and zinc oxide acidified with sulfamic or sulfuric acid. Mixtures of the aforementioned compounds may also be employed.

The catalyst is present from about 0.01% to about 2% (calculated e.g. as zinc or other metal ion) based on the combined weight of charged reactants. Preferably, the amount of catalyst charged will range from about 0.01 to 1%. Higher amounts of catalysts, particularly those containing zinc, are undesirable due to their detrimental effect on product qualities such as color.

Unexpectedly, it has been discovered that when zinc catalysts are employed in the DEFI reaction, pH plays a critical role in product yield. Above about pH 2.5, yield begins to decrease. The phenomena is most acute where catalyst is present at lower concentrations, e.g., 0.05%. Below pH 2.0, yields appear to be stable. Corrosion of the stainless steel reactor, however, becomes a problem when operating reactions at low pH. Experiments indicate that stainless steel corrosion in the DEFI process is surprisingly minimal between about pH 2.0 and 2.5. Below pH 2.0, corrosion becomes severe. Consequently, the optimum pH of the reaction is between about 2.0 and 2.5.

While it is beneficial to use the acidic soluble zinc catalysts to increase reaction rates and prevent equipment corrosion, acid catalysts do have some other detrimental features. During the severe conditions of stripping, acid catalysts cause darkening of the product. Neutralization with an alkaline quenching material reduces or eliminates darkening and deterioration of product.

An additional aspect of this invention involves the elimination of the traditional stripping step, to remove excess $C_5$–$C_{12}$ fatty acids, following esterification. Elimination of this step produces usable product in a much shorter time and requires less equipment. Substantial cost reductions are achieved thereby.

The conventional zinc oxide promoted DEFI process utilizes coconut fatty acid to sodium isethionate ratios of 1.35:1 and higher. These high fatty acid ratios are needed to speed reaction rates and favor coconut fatty acids over DEFI transesterification with stearic acid. With the new "fast" catalysts and alkaline quench step, it has been found that ratios of 1.19:1 or less coconut fatty acid to sodium isethionate can be utilized. Not only are the prior detrimental aspects avoided but definite advantages accrue with the lower ratios. A major benefit is that stripping excess coconut fatty acid is no longer required. A step is thereby avoided.

When reduced reactant ratios (1.19:1 or less) are utilized, fatty acid mixtures, that co-distill with liberated water of esterification, must be recycled into the reaction mass. The reaction proceeds in the conventional manner as described in U.S. Pat. No. 3,320,292 with agitation in a non-oxidizing atmosphere of nitrogen or carbon dioxide. Reaction temperatures range from 200° C. to 260° C. with 233° C. being standard. Volatile fatty acid and water are distilled from the reaction mass, condensed and separated. Fatty acid is recycled back to the reaction mass. With a conventional catalyst such as zinc oxide, it is preferable to add stearic acid at the end of the reaction to minimize transesterification. However, some stearic acid may have to be added earlier to prevent foam-over or reduce batch viscosity. Addition of stearic acid may be done incrementally or continuously. If an acidic catalyst like zinc isethionate is to be used without subsequent neutralization, stearic acid may be added at any time. Yet, where transesterification is to be minimized, it is best to delay addition of stearic acid until the desired conversion is achieved. A caustic is then added prior to or along with stearic acid to neutralize the catalyst.

A variation of the general method utilizes the traditional 1.35:1 or higher ratio of coconut fatty acid to sodium isethionate. However, in a departure from the conventional procedure distilled fatty acids are not recycled into the reaction mass.

In both no-strip methods, higher molecular weight fatty acid, primarily stearic acid, is added during the reaction. Time and manner of addition is dictated by catalyst choice and reaction physics. With the no-strip methods, choice of catalysts effects chain length distribution of the isethionate ester product. When using a conventional catalyst such as zinc oxide, delaying the addition of stearic acid until 90% conversion is obtained will produce an isethionate ester virtually identical to that produced by the conventional process. Earlier addition of stearic acid will bring about some deviation in the chain length distribution of the product; in particular, a higher proportion of $C_{16}$ and $C_{18}$ esters but lower proportions of $C_{12}$ esters. This is caused by transesterification between the higher molecular weight fatty acids and the isethionate ester.

Transesterification equilibrium is reached very rapidly with the more active acidic catalysts such as the soluble zinc salts. Here, the same reaction product is obtained regardless of when stearic acid is added. Transesterification can be minimized, however, by adding alkaline material prior to or during addition of stearic acid. Of course, this is done at the end of the reaction when acceptable conversion has been obtained. Early addition of caustic will prevent the reaction from proceeding any further.

The following examples will more fully illustrate the embodiments of this invention. All parts, percentages and proportions referred to herein and in the appended claims are by weight unless otherwise illustrated.

EXAMPLE I

As a control, a mixture of 500 g. coconut fatty acid and 273 g. sodium isethionate (relative ratio 1.35:1 coconut fatty acid to isethionate) was charged to a liter reaction vessel and stirred. Additionally, 72 g. of water were added to simulate a slurry of sodium isethionate typical of that encountered in commercial processes. To this mixture, 0.87 g. ZnO were added. The vapor space was filled with nitrogen introduced by bubbling through the reaction mixture. Nitrogen sparging was done throughout the reaction. Nitrogen aided in sweeping volatile fatty acid and water components into the water condenser. Located below the condenser was a Dean-Stark trap for collection and measurement of condensate.

The reactor was heated electrically to 233° C., by which time the water initially charged had boiled-off from the reaction mixture. When the reaction mass rose to a temperature of 221° C., timing of the reaction commenced. A total of 100 g. water were removed by distillation. Fatty acids that had co-distilled from the reactor were recycled back to the reaction mass. Toward the end of the esterification, to prevent foam-over and reduce batch viscosity, 126 g. stearic acid were added to the batch.

Samples were taken every fifteen minutes for hyamine titration (described in "ASTM Standards, Part X", 1961, pages 1099-1101, using di-isobutyl phenoxyethoxyethyl, dimethyl benzyl ammonium chloride dihydrate). The amount of isethionate ester produced was then calculated, with percent theoretical yield determined on the basis of a theoretically possible 1.84 moles. From this data, the kinetic profile set forth in Table I was obtained.

TABLE 1

| Reaction Yield in the Presence of Zinc Oxide | | |
| --- | --- | --- |
| Time (Minutes) | Temperature °C. | Conversion % |
| 15 | 233 | 6.5 |
| 30 | 233 | 35.2 |
| 45 | 233 | 61.5 |
| 60 | 233 | 73.4 |
| 75 | 233 | 78.9 |
| 90 | 233 | 79.5 |

Upon completion of esterification, excess $C_5$–$C_{12}$ fatty acids were removed by distillation. This step, known as the stripping operation, was divided into two phases. In the first, a vacuum of 10–20 inches Hg. was applied to the reaction mixture and heating maintained at 200°–260° C. As the $C_5$–$C_{12}$ fatty acids were distilled, the reaction mass became thicker and foamed. The first phase of stripping continued for about 15 minutes. In the final stripping phase, the vacuum was raised to 29 inches Hg. for an additional 40 minutes after 126 g. of stearic acid were added. This procedure removed most of the lower molecular weight fatty acids through distillation.

EXAMPLE II

The following example illustrates the no strip method employing a low mole ratio, coconut fatty acid to sodium isethionate of 1.10:1.0. A reactor was charged with 415 g. coconut fatty acid, 273 g. sodium isethionate and 4 g. zinc isethionate. The temperature was raised to 248° C. and maintained there for 60 minutes while stirring. Nitrogen was introduced to blanket the reactor space. Sparging of nitrogen was continued throughout the reaction period.

Water of esterification was continuously removed by collection in a Dean-Stark trap. Any $C_5$–$C_{12}$ fatty acids that co-distilled with water during the reaction were recycled into the reactor. A total of 60 g. water was recovered within the first hour. Thereafter, 126 g. stearic acid and 2.0 g. sodium hydroxide were added to the reaction mixture. Subsequent cooking at 240°–245° C. for a further 60 minutes afforded an additional 4 g. water. The yield was 87.4%. Vacuum stripping was not applied in this experiment. Soap bar firmness and latherability were excellent in the resultant product.

EXAMPLE III

The experiment was repeated except that a 1.19:1.0 ratio coconut fatty acid to sodium isethionate was utilized. Vacuum stripping was similarly eliminated from this experiment and temperature was lowered to 236° C. The resultant product was obtained in 84.4% yield. The resultant soap had both good latherability and bar firmness.

EXAMPLE IV

The following illustrates the no strip method using the conventional 1.35:1 ratio, coconut fatty acid to sodium isethionate, wherein distillate $C_5$–$C_{12}$ fatty acids were not recycled. The reactor is charged with 500 g. coconut fatty acid and 273 g. sodium isethionate. As the temperature is raised to 233° C., 4 g. sodium isethionate catalyst is added to the vessel. Temperature is maintained at 233°–243° C. for 1 hour. Water by-product is continuously distilled from the reaction mass. Co-distillate low molecular weight $C_5$–$C_{12}$ fatty acids are not recycled into the reaction as done in the conventional method. After 60 minutes, 126 g. stearic acid and 2.0 g. sodium hydroxide are added to the reaction mass. Heat is maintained at 240°–245° C. for an additional hour. Unlike the conventional process, the fatty acid portion is not recycled nor the vacuum-stripping step practiced. Nevertheless, a soap product of good bar firmness and latherability is achieved.

EXAMPLE V

A group of reactions were conducted to demonstrate the effectiveness of catalyst neutralization in hindering transesterification. They employed the same method as outlined in Example I except that 2.0 grams NaOH was added along with the stearic acid.

These tests were performed with zinc isethionate and with sulfamic acid as catalysts. The effect of catalyst deactivation is shown in Table 2.

A pronounced effect on transesterification was seen between the less active zinc oxide catalyst and the faster zinc isethionate and sulfamic acid. Transesterification is evidenced by the higher relative proportions of $C_{16}$ and $C_{18}$ esters in the reaction product. Since these esters adversely effect lather in detergent bars, it is important to minimize them. Quenching the catalyst with sodium hydroxide for both zinc isethionate and sulfamic acid catalyzed DEFI reactions reduced the $C_{16}$ and $C_{18}$ components in the ester product. Soap bar firmness, for easier processing, and latherability were observed improvements (see Table 2).

TABLE 2
Effect Of Catalyst Deactivation On Chain Length Distribution In Isethionate Ester

| | ZnO No NaOH | Zinc Isethionate No NaOH | Zinc Isethionate 2 g NaOH added | Sulfamic Acid No NaOH | Sulfamic Acid 2 g NaOH added |
|---|---|---|---|---|---|
| % $C_8$ | 4.0 | 3.8 | 5.3 | 1.7 | 5.9 |
| % $C_{10}$ | 5.5 | 4.7 | 5.6 | 3.0 | 6.0 |
| % $C_{12}$ | 43.6 | 40.0 | 45.1 | 32.0 | 48.4 |
| % $C_{14}$ | 15.0 | 14.9 | 16.3 | 14.9 | 17.8 |
| % $C_{16}$ | 14.5 | 18.6 | 13.7 | 22.3 | 11.2 |
| % $C_{18}$ | 13.9 | 16.9 | 12.6 | 23.5 | 9.8 |
| Lather: | excellent | fair | excellent | fair | excellent |
| Bar Firmness: | excellent | fair | excellent | fair | excellent |

EXAMPLE VI

The following example illustrates the effect of pH on the percent conversion to DEFI in zinc salt catalyzed systems.

A reactor was charged with a 1.35:1.0 ratio of coconut fatty acid to sodium isethionate as in Example I. Zinc sulfate, prepared from the acidification of zinc oxide with sulfuric acid, was utilized as the catalyst. A 1 hour reaction was performed at 235°–245° C. Various pH enviroments at three different zinc levels were evaluated. Results are found in Table 3.

TABLE 3
Percent Yield - $ZnSO_4$ - 1 Hour Reaction

| | pH (100° C.) | | | | |
|---|---|---|---|---|---|
| % Zn | 2.0 | 2.3 | 2.5 | 2.7 | 3.2 |
| .05% | 90.4 | 89.5 | 84.9 | 78.2 | 55.9 |
| .10% | 89.9 | 90.3 | 84.4 | 78.4 | 71.4 |
| .18% | 88.3 | 89.9 | 92.1 | 87.3 | 80.3 |

At about pH 2.5 and higher, percent conversion to DEFI falls. Although the effect is most pronounced at lower zinc sulfate concentrations, some yield reduction occurs at all zinc levels. Below pH 2.5, yields appear to be independent of zinc sulfate content. For zinc oxide, a similar phenomena was observed. For example, 0.10% zinc oxide under the conditions of Example I, pH adjusted with a mineral acid, achieved yields of 90.1%, 86.2% and 76.2% at pH 2.3, 2.7 and 2.8, respectively.

When operating at low pH, corrosion of reactor metal surfaces is of considerable concern. In order to determine corrosion, a test sample of a half-moon shaped stirrer blade made of stainless steel type 316 was utilized. The blade had a 1.5 mm thickness, a 20 mm radius and an approximate surface area of 12.4 $cm^2$. Corrosiveness was measured by taking the weight of the 316 stainless steel blade before and after DEFI runs. After each run, the blade was washed with water, rinsed with acetone and finally dried before weighing The blade was re-polished with a fine emery paper between different series of corrosion tests. Surprisingly, at pH 2.3 in the 0.05% zinc sulfate catalyzed reaction, corrosion appeared minimal exhibiting a weight loss of 0.2 mg/34 $cm^2$. Below pH 2.0, corrosion becomes a greater problem. Above pH 2.5, corrosion appears to be steady from 0.2 to 0.3 mg/34 $cm^2$. For comparative purposes, the weight loss in the absence of any catalyst was 0.59 mg/34 $cm^2$.

EXAMPLE VII

The procedure illustrated in Example I was repeated using various zinc compounds to catalyze the reaction. These included zinc sulfate, zinc sulfamate and zinc oxide acidified with sulfamic acid. Results are set forth in Table 4.

Whereas zinc oxide attained a 73.4% conversion after 60 minutes, the zinc salts of Table 4 reach conversions ranging from 80.0 to 87.3% in the same time span.

TABLE 4
Reaction Yields in Presence of Various Zinc Catalysts

| Catalyst | Weight Percent Catalyst | Reaction Time Minutes | Reaction Temperature °C. | Conversion % |
|---|---|---|---|---|
| $ZnSO_4.H_2O$ | 0.05 | 60 | 233 | 87.3 |
| $ZnO/HSO_3NH_2$ | 0.05 | 60 | 233 | 81.6 |
| $Zn(NH_2SO_3)_2$ | 0.05 | 60 | 233 | 80.0 |

The foregoing description and examples illustrate selected embodiments of the present invention. In light thereof, various modifications will be suggested to one skilled in the art, all of which are within the spirit and purview of this invention.

What is claimed is:

1. A method is disclosed of preparing a compound of the formula $RCOOR'SO_3M$, wherein R is a $C_5$–$C_{18}$ alkyl group, R' is selected from the group consisting of divalent $C_2$–$C_4$ alkylene, $C_6$–$C_8$ aryl and $C_7$–$C_8$ alkylaryl radicals and M is an alkali metal cation, the process comprising:
   (a) heating at 200° to 260° C. a first mixture of $C_5$–$C_{16}$ monocarboxylic acid with a hydroxy sulfonate of the formula $HOR'SO_3M$, in a mole ratio of 1.01:1 to 2:1, in the presence of a catalyst;
   (b) removing liberated water of esterification from the reaction mass and when the desired conversion to $RCOOR'SO_3M$ is achieved;
   (c) quenching the catalyst with an effective amount to neutralize the catalyst of an alkaline compound; and
   (d) adding a higher molecular weight $C_{15}$–$C_{24}$ fatty acid to the reaction mixture subsequent or simultaneous with addition of alkaline catalyst quencher.

2. A method according to claim 1 wherein the catalyst is selected from the group consisting of multivalent metal ion organic or inorganic salts, strong acids and mixtures thereof.

3. A method according to claim 2 wherein the catalyst is a zinc salt.

4. A method according to claim 3 wherein the pH is maintained between about 2.0 to about 2.5.

5. A method according to claim 2 wherein the catalyst is derived from a mixture of zinc oxide and an organic sulfonic acid.

6. A method according to claim 2 wherein the catalyst is zinc isethionate.

7. A method according to claim 3 wherein the zinc catalyst is selected from the group consisting of zinc sulfate, zinc sulfamate and zinc oxide acidified with sulfamic or sulfuric acid, and mixtures thereof.

8. A method according to claim 1 wherein a mixture of free $C_5$–$C_{16}$ fatty acids is continously supplied to the reaction mass during the course of esterification at approximate rates and proportions at which the fatty acids are vaporized.

9. A method according to claim 1 wherein the mole ratio of monocarboxylic acid to hydroxy sulfonate is from 1.35:1 to 1.5:1 or higher, further characterized in that the $C_5$–$C_{16}$ fatty acid co-distillate during the course of esterification is not recycled back into the reaction mass and a final stripping step is eliminated.

10. A method according to claim 8 wherein the mole ratio of carboxylic acid to hydroxy sulfonate is about 1.01:1 to 1.19:1, further characterized in that a final stripping step is eliminated.

11. A method according to claim 1 wherein the alkaline compound is selected from the group consisting of alkali metal hydroxides, ammonia, carbonate and bicarbonate salts, and mixtures thereof.

* * * * *